(12) United States Patent
Miller (10) Patent No.: US 8,505,370 B2
(45) Date of Patent: Aug. 13, 2013

(54) METHOD AND SYSTEM TO DIAGNOSE EXHAUST GAS SENSOR DETERIORATION

(75) Inventor: Ryan A. Miller, Laguna Hills, CA (US)

(73) Assignee: Toyota Motor Engineering & Manufacturing Norh America, Inc., Erlanger, KY (US)

( * ) Notice: Subject to any disclaimer, the term of this patent is extended or adjusted under 35 U.S.C. 154(b) by 297 days.

(21) Appl. No.: 12/952,032

(22) Filed: Nov. 22, 2010

(65) Prior Publication Data

US 2012/0125090 A1  May 24, 2012

(51) Int. Cl.
  *G01M 15/10* (2006.01)
(52) U.S. Cl.
  USPC ...................................................... 73/114.69
(58) Field of Classification Search
  USPC ................... 73/23.31, 23.32, 114.69, 114.71, 73/114.72, 114.73
  See application file for complete search history.

(56) References Cited

U.S. PATENT DOCUMENTS

| | | | |
|---|---|---|---|
| 4,938,194 A | 7/1990 | Kato et al. | |
| 5,048,490 A | 9/1991 | Nakaniwa | |
| 5,747,668 A | 5/1998 | Cianciara | |
| 5,804,700 A | 9/1998 | Kwon et al. | |
| 5,927,260 A | 7/1999 | Kishimoto et al. | |
| 5,979,160 A | 11/1999 | Yashiki et al. | |
| 6,481,273 B2 | 11/2002 | Maloney | |
| 6,880,380 B2 | 4/2005 | Nagashima et al. | |
| 6,920,751 B2 | 7/2005 | Yasui et al. | |
| 6,976,382 B2 | 12/2005 | Kadowaki et al. | |
| 7,021,300 B2 | 4/2006 | Maki et al. | |
| 7,117,664 B2 | 10/2006 | Takaku et al. | |
| 7,142,976 B2 | 11/2006 | Inoue et al. | |
| 7,171,298 B2 | 1/2007 | Feucht et al. | |
| 7,286,926 B2 | 10/2007 | Gotoh et al. | |
| 7,387,011 B2 | 6/2008 | Fujiki et al. | |
| 7,441,554 B2 | 10/2008 | Nakagawa et al. | |
| 7,549,284 B2 | 6/2009 | Iihoshi et al. | |
| 7,739,868 B2 | 6/2010 | Chino et al. | |
| 2006/0037305 A1* | 2/2006 | Nagashima et al. | ............ 60/276 |
| 2008/0154528 A1* | 6/2008 | Iwazaki | ........................ 702/100 |

FOREIGN PATENT DOCUMENTS

| | | |
|---|---|---|
| JP | 2004245604 | 9/2004 |
| JP | 2008203140 | 9/2008 |
| JP | 2009167987 | 7/2009 |

* cited by examiner

*Primary Examiner* — Eric S McCall
(74) *Attorney, Agent, or Firm* — Snell & Wilmer, LLP (57) ABSTRACT

In a method and system to diagnose exhaust gas sensor deterioration, an automobile includes an exhaust gas system. The exhaust gas system has a fuel delivery system, an engine, a catalytic converter, an exhaust gas sensor, a processor, and/or a memory. The fuel delivery system supplies fuel which is combined with air to form a mixture combusted by the engine to generate exhaust. The processor controls the air-fuel ratio of the mixture based on the air-fuel ratio data of the exhaust detected by the exhaust gas sensor. The catalytic converter reduces pollutants in the exhaust. The processor analyzes the air-fuel ratio data to determine one or more time constants of a step response for rich to lean fuel operations and/or lean to rich fuel operations. The processor compares the time constants to a predetermined time constant threshold to determine if the exhaust gas sensor has malfunctioned.

19 Claims, 4 Drawing Sheets

METHOD AND SYSTEM TO DIAGNOSE EXHAUST GAS SENSOR DETERIORATION

BACKGROUND

1. Field

The present invention relates to a method and system to diagnose exhaust gas sensor deterioration.

2. Description of the Related Art

A conventional automobile includes an engine which combusts a mixture to generate an exhaust. The composition of the exhaust is regulated by governmental agencies for pollutants. To reduce the amount of pollutants, the air-fuel ratio of the mixture can be controlled. The conventional automobile utilizes an exhaust gas sensor to determine air-fuel ratio data for an exhaust of an engine. Such air-fuel ratio data can determine adjustments to the air-fuel ratio of a mixture supplied to the engine. Such adjustments, however, can be incorrect when the exhaust gas sensor malfunctions due to deterioration.

Conventional methods to detect exhaust gas sensor malfunctions have utilized threshold switching based on the air-fuel ratio data. However, such methods cannot use fixed gain and fixed frequency because the air-fuel ratio data may not cross the necessary thresholds as the sensor response slows.

Furthermore, governmental agencies are increasingly demanding that malfunctions be detected not just for the overall operations of the exhaust gas sensor, but in a more finite manner, such as during lean to rich fuel operations or rich to lean fuel operations. Conventional methods, however, are unable to parse the malfunctions in such a manner.

In addition, conventional methods generally require that the automobile be at a constant speed for a large number of cycles, such as 12 output cycles. With the large number of cycles, there is an increased chance that the method will be interrupted due to a change in automobile speed. This reduces the amount of tests that can be performed and/or increases the number of attempts that must be made in order to diagnose the exhaust gas sensor deterioration, both of which are undesirable.

Thus, there is a need for a method and system to diagnose exhaust gas sensor deterioration.

SUMMARY

The present invention relates to a method and system to diagnose exhaust gas sensor deterioration. In one embodiment, the present invention is an automobile including an exhaust gas system. The exhaust gas system can include a fuel delivery system, an engine, a catalytic converter, an exhaust gas sensor, a processor, and/or a memory. The fuel delivery system can supply fuel to the engine which can be combined with air to form a mixture which can be combusted by the engine to generate an exhaust.

The air-fuel ratio of the mixture can be controlled by the processor based on the air-fuel ratio data for the exhaust as detected by the exhaust gas sensor. The catalytic converter can receive the exhaust, and chemical reactions can be performed in the catalytic converter on the exhaust to reduce pollutants. The processor can analyze the air-fuel ratio data to determine one or more time constants of a step response for rich to lean fuel operations and/or lean to rich fuel operations. The processor can compare the time constants to a predetermined time constant threshold to determine if the exhaust gas sensor has malfunctioned or not.

Advantageously, the processor detects the deterioration of the exhaust gas sensor using less output cycles, reducing the number of times that such analysis is interrupted. In addition, the processor can determine exhaust gas sensor deterioration for not just the overall operations of the exhaust gas sensor, but also separately for the lean to rich fuel operation and the rich to lean fuel operation.

In one embodiment, the present invention is a method for determining an exhaust gas sensor malfunction including detecting, using an exhaust gas sensor, air-fuel ratio data of an exhaust of an engine, the air-fuel ratio data including a starting air-fuel ratio and an actual air-fuel ratio; determining, using a processor, a time constant of a step response for the exhaust gas sensor from the air-fuel ratio data, the time constant being determined based on a difference between a target air-fuel ratio and the actual air-fuel ratio and a difference between the target air-fuel ratio and the starting air-fuel ratio, and comparing, using the processor, the time constant with a predetermined time constant threshold, and determining that the exhaust gas sensor has malfunctioned when the time constant is less than the predetermined time constant threshold.

In another embodiment, the present invention is a method for determining an exhaust gas sensor malfunction including generating, using a fuel delivery system, a plurality of output cycles from an engine, detecting, using an exhaust gas sensor, air-fuel ratio data of an exhaust of the engine, the air-fuel ratio data including a starting air-fuel ratio, and an actual air-fuel ratio, determining, using a processor, a time constant of a step response for the exhaust gas sensor from the air-fuel ratio data, wherein the time constant is determined using a difference between a target air-fuel ratio and the actual air-fuel ratio divided by a difference between the target air-fuel ratio and the starting air-fuel ratio, and comparing, using the processor, the time constant with a predetermined time constant threshold, and determining that the exhaust gas sensor has malfunctioned when the time constant is less than the predetermined time constant threshold.

In another embodiment, the present invention is an automobile including an engine generating an exhaust, a fuel delivery system connected to the engine and configured to generate a plurality of output cycles from the engine, an exhaust gas sensor configured to detect air-fuel ratio data of the exhaust, the air-fuel ratio data including a starting air-fuel ratio, and an actual air-fuel ratio, and a processor receiving the air-fuel ratio data. The processor is configured to determine a time constant of a step response for the exhaust gas sensor from the air-fuel ratio data, wherein the time constant is determined using a difference between a target air-fuel ratio and the actual air-fuel ratio divided by a difference between the target air-fuel ratio and the starting air-fuel ratio, compare the time constant with a predetermined time constant threshold, and determine that the exhaust gas sensor has malfunctioned when the time constant is less than the predetermined time constant threshold.

BRIEF DESCRIPTION OF THE DRAWINGS

The features, obstacles, and advantages of the present invention will become more apparent from the detailed description set forth below when taken in conjunction with the drawings, wherein.

DETAILED DESCRIPTION

Apparatus, systems and methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

Figure 1:
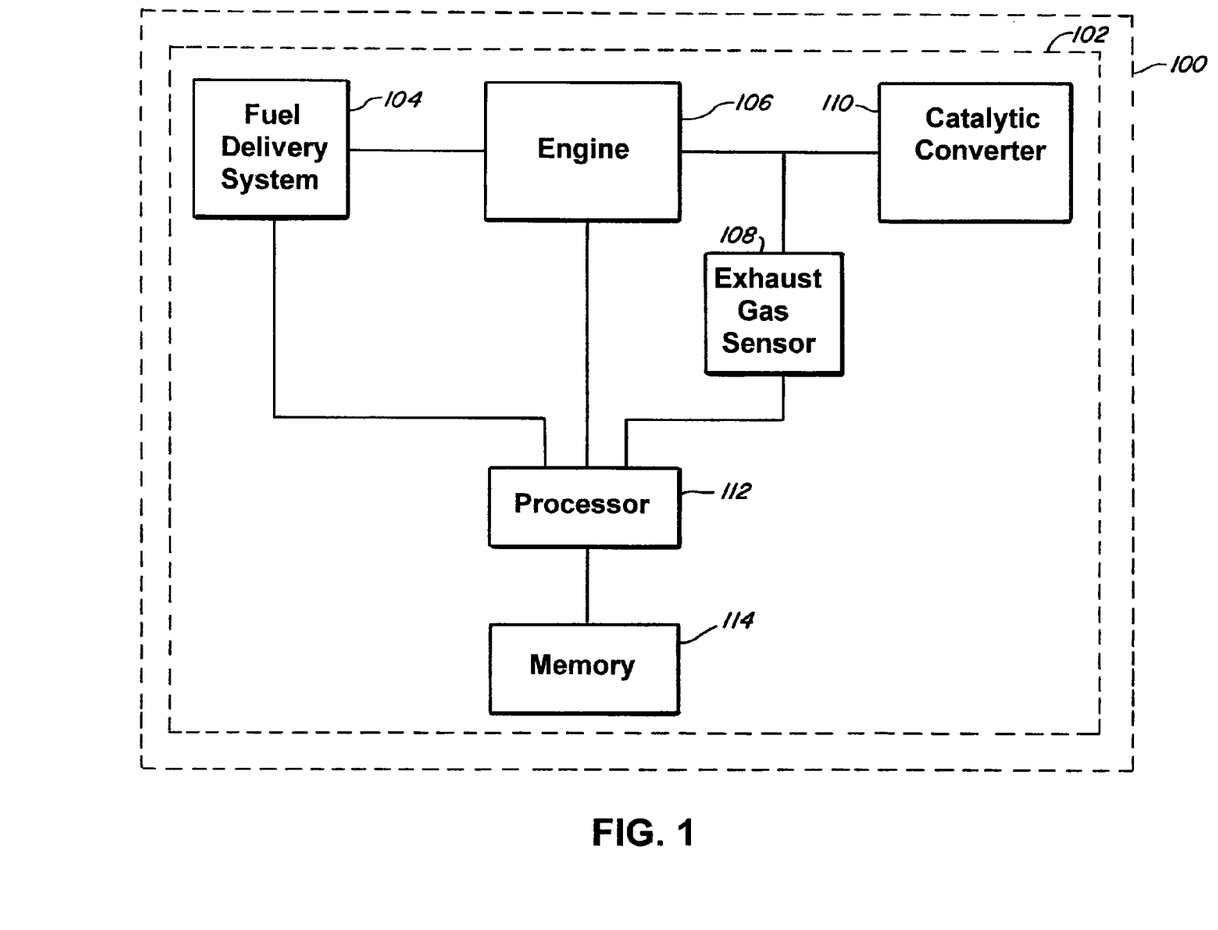
FIG. 1 is a box diagram of an automobile including an exhaust system according to an embodiment of the present invention.

In one embodiment, the present invention includes an automobile 100. The automobile 100 can include, for example, an exhaust system 102. The exhaust system 102 can include, for example, a fuel delivery system 104, an engine 106, an exhaust gas sensor 108, a catalytic converter 110, a processor 112, and/or a memory 114.

The fuel delivery system 104 is connected, for example, to the engine 106 and/or the processor 112. The fuel delivery system 104 can control, for example, an amount of fuel delivered to the engine 106. The amount of fuel delivered to the engine 106 can control, for example, an air-fuel ratio of a mixture combusted by the engine 106. This can control, for example, an output cycle of the engine 106.

The engine 106 is connected, for example, to the fuel delivery system 104, the catalytic converter 110, and/or the processor 112. The engine 106 can, for example, generate exhaust from combusting the fuel delivered by the fuel delivery system 104. The exhaust can include, for example, a plurality of output cycles, with each output cycle including a maximum air-fuel ratio and a minimum air-fuel ratio.

The exhaust gas sensor 108 is located between the engine 106 and the catalytic converter 110 and can also be connected to the processor 112. The exhaust gas sensor 108 can analyze the exhaust to determine air-fuel ratio data of the exhaust. The air-fuel ratio data can include, for example, a starting air-fuel ratio, and an actual air-fuel ratio for portions of each output cycle. Each output cycle can also include, for example, a rich to lean fuel operation and a lean to rich fuel operation. Each of the rich to lean and lean to rich fuel operations can include a maximum and a minimum air-fuel ratio.

The catalytic converter 110 is connected, for example, to the engine 106, and/or the exhaust gas sensor 108. The catalytic converter 110 receives the exhaust from the engine 106 and performs, for example, chemical reactions on the exhaust to reduce pollutants in the exhaust.

The memory 114 is connected, for example, to the processor 112. The memory 114 can store, for example, air-fuel ratio data for the exhaust. In addition, the memory 114 can store, for example, an optimal air-fuel ratio data. The optimal air-fuel ratio data can indicate air-fuel ratio data which should be detected by the exhaust gas sensor 108. The optimal air-fuel ratio data can include, for example, a target air-fuel ratio. In addition, the memory 114 can store, for example, a predetermined time constant threshold, which can be used to determine when the exhaust gas sensor 108 has deteriorated or malfunctioned.

The processor 112 can be connected, for example, to the fuel delivery system 104, the engine 106, the exhaust gas sensor 108, the catalytic converter 110, and/or the memory 114. The processor 112 can control the fuel delivery system 104 to deliver fuel to the engine 106 in a manner which causes the engine 106 to generate an output cycle. The processor 112 can receive the air-fuel ratio data from the exhaust gas sensor 108 and compare it with an optimal air-fuel ratio data which can be stored in the memory 114. The processor 112 can analyze the air-fuel ratio data to determine a maximum air-fuel ratio and a minimum air-fuel ratio.

Such information can be used to determine whether the exhaust gas sensor 108 has deteriorated or not, and the extent of any such deterioration. Furthermore, such information can determine whether the exhaust gas sensor has deteriorated for specific fuel operations of the exhaust gas sensor, such as a lean to rich fuel operation, or a rich to lean fuel operation.

For example, using the maximum air-fuel ratio and the minimum air-fuel ratio along with the target air-fuel ratio, the processor 112 can determine a time constant for a step response for the exhaust gas sensor 108 for one or more fuel operations, such as a rich to lean fuel operation and/or a lean to rich fuel operation. The time constant for the rich to lean fuel operation and/or the lean to rich fuel operation can be compared with a predetermined time constant threshold, and if the time constant for the rich to lean fuel operation and/or the lean to rich fuel operation is greater than the predetermined time constant threshold, then the exhaust gas sensor 108 has malfunctioned (such as through deterioration) and may need to be replaced and/or repaired.

In one embodiment, the step response can be seen in the equation $1-e^{-t\phi}$ where $\phi$ is a time constant. As previously noted, the time constant for a lean to rich fuel operation ($\phi_{LR}$) and a time constant for a rich to lean fuel operation ($\phi_{RL}$) can be calculated.

The time constant for the lean to rich fuel operation can be represented by the formula $$\phi_{LR} = \frac{-\ln\left(\frac{|\lambda_{RTarget} - \lambda_{min}|}{\lambda_{max} - \lambda_{RTarget}}\right)}{\Delta t_{LR}},$$

where $\phi_{LR}$ is the time constant for the lean to rich fuel operation, $\lambda_{RTarget}$ is the target air-fuel ratio, $\lambda_{min}$ is the minimum air-fuel ratio, $\lambda_{max}$ is the maximum air-fuel ratio, and $\Delta t_{LR}$ is a time period between detection of the $\lambda_{min}$ and the $\lambda_{max}$.

In the lean to rich fuel operation, the target air-fuel ratio is a minimum air-fuel ratio for the optimal air-fuel ratio data. That is, the target air-fuel ratio is the minimum air-fuel ratio that the exhaust gas sensor 108 should be detecting in a lean to rich fuel operation because the fuel delivery system 104 is attempting to enrich the air-fuel ratio (thus decreasing the air-fuel ratio).

In addition, in the lean to rich fuel operation, the starting air-fuel ratio is the maximum air-fuel ratio $\lambda_{max}$ of the air-fuel ratio data and the actual air-fuel ratio is the minimum air-fuel ratio $\lambda_{min}$ of the air-fuel ratio data because the air-fuel ratio indicated by the air-fuel ratio data should decrease in a lean to rich operation.

The time constant for a rich to lean fuel operation can be represented by the formula $$\phi_{RL} = \frac{-\ln\left(\frac{|\lambda_{max} - \lambda_{LTarget}|}{\lambda_{LTarget} - \lambda_{min}}\right)}{\Delta t_{RL}},$$

where $\phi_{RL}$ is the time constant for a portion of one of the output cycles corresponding to a rich to lean fuel operation by a fuel delivery system $\lambda_{LT\,arg\,et}$ is the target air-fuel ratio, $\lambda_{min}$ is the minimum air-fuel ratio, $\lambda_{max}$ is the maximum air-fuel ratio, and $\Delta t_{RL}$ is a time period between detection of the $\lambda_{min}$ and the $\lambda_{max}$. In the rich to lean fuel operation, the target air-fuel ratio is a maximum air-fuel ratio for the optimal air-fuel ratio data.

In the rich to lean fuel operation, the target air-fuel ratio is a maximum air-fuel ratio for the optimal air-fuel ratio data. That is, the target air-fuel ratio is the maximum air-fuel ratio that the exhaust gas sensor 108 should be detecting in a rich to lean fuel operation because the fuel delivery system 104 is attempting to lean the air-fuel ratio (i.e., increase the air-fuel ratio).

In addition, in the rich to lean fuel operation, the starting air-fuel ratio is the minimum air-fuel ratio $\lambda_{min}$ of the air-fuel ratio data and the actual air-fuel ratio is the maximum air-fuel ratio $\lambda_{max}$ of the air-fuel ratio data because the air-fuel ratio indicated by the air-fuel ratio data should increase in a rich to lean operation.

Figure 2:
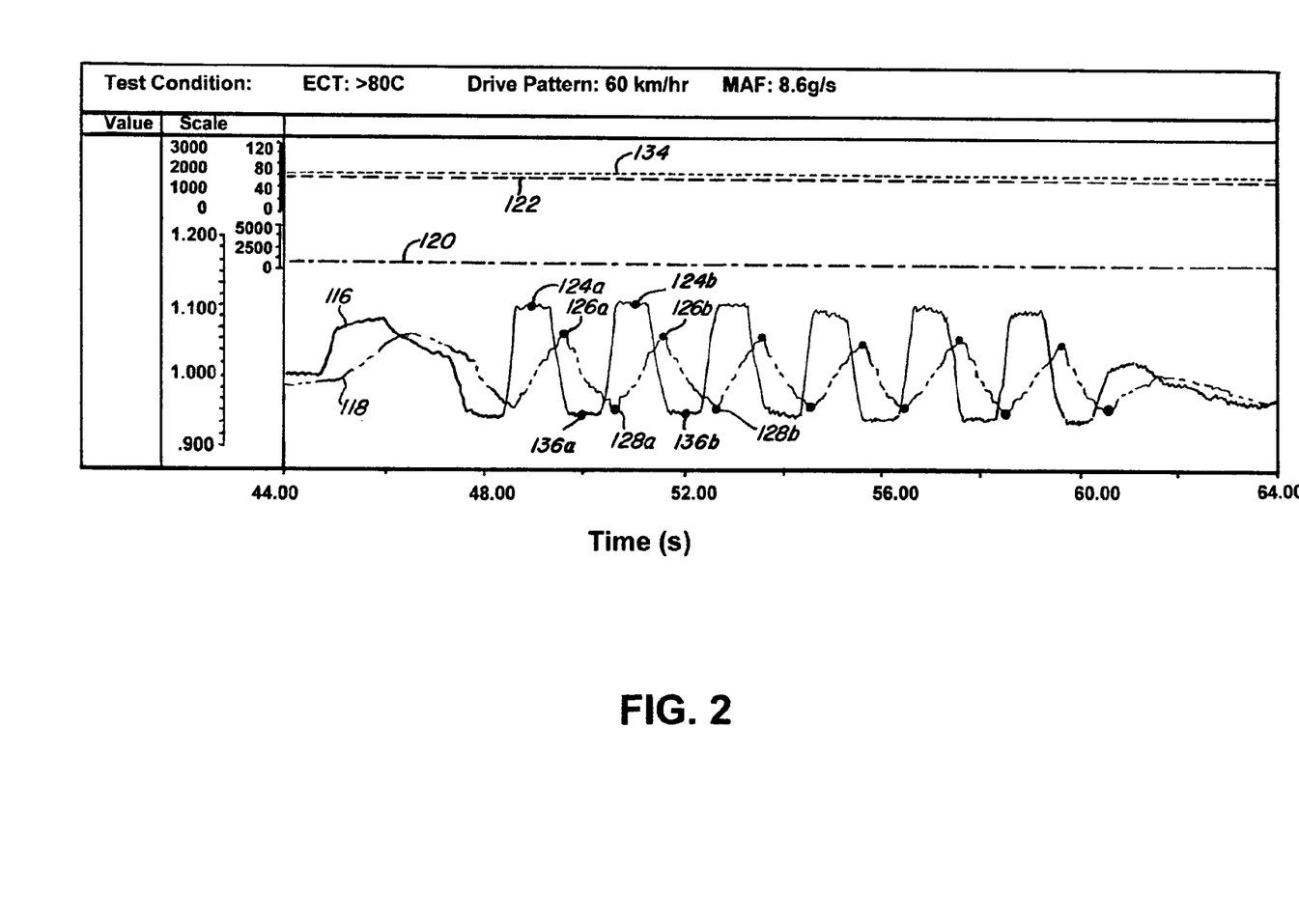
FIG. 2 depicts a graph including output cycles of an engine according to an embodiment of the present invention.

This can be seen, for example, in FIG. 2. In FIG. 2, the automobile 100 is operating at a constant speed (km/hr) as indicated by a curve 122 and at a constant engine speed (RPM) as indicated by a curve 134. Furthermore, the automobile 100 includes a constant mass air flow (g/s) as indicated by a curve 120. A curve 116 represents an optimal air-fuel ratio data, while a curve 118 represents the air-fuel ratio data detected by the exhaust gas sensor 108. The curve 116 and the curve 118 represent the air-fuel ratio data multiplied by the stoichiometric air-fuel ratio for gasoline (approximately 14.7). However, since the stoichiometric air-fuel ratio is merely a constant, the description of the air-fuel ratio data will be described as incorporating the stoichiometric air-fuel ratio.

Points 124a, 124b, 136a, and 136b represent, for example, maximum and minimum air-fuel ratios of the optimal air-fuel ratio data. For example, the points 124a and 124b can be maximum air-fuel ratios of the optimal air-fuel ratio data while the points 136a and 136b can be minimum air-fuel ratios of the optimal air-fuel ratio data. Likewise, points 126a and 126b represent maximum air-fuel ratios for the air-fuel ratio data detected by the exhaust gas sensor 108 and the points 128a and 128b represent minimum air-fuel ratios for the air-fuel ratio data detected by the exhaust gas sensor 108.

Moving from point 126a to point 128a represents, for example, a lean to rich fuel operation, while moving from point 126b to point 128b represents, for example, a rich to lean fuel operation. In addition, a lean to rich fuel operation and a rich to lean fuel operation can be combined to represent a single output cycle for the engine 106.

For example, to calculate the time constant for a rich to lean fuel operation $\phi_{RL}$ from point 128a to point 126b, the target air-fuel ratio $\lambda_{LT\,arg\,et}$, the minimum air-fuel ratio $\lambda_{min}$, the maximum air-fuel ratio $\lambda_{max}$, and the time period $\Delta t_{RL}$ between detection of the minimum air-fuel ratio $\lambda_{min}$ and the maximum air-fuel ratio $\lambda_{max}$ can be utilized. The target air-fuel ratio $\lambda_{LT\,arg\,et}$ can be indicated, for example, by the point 124b representing the maximum air-fuel ratio of the optimal air-fuel ratio data in the curve 116. The minimum air-fuel ratio $\lambda_{min}$ can be, for example, a starting air-fuel ratio represented by the point 128a. The maximum air-fuel ratio $\lambda_{max}$ can be, for example, an actual air-fuel ratio represented by the point 126b. The time period $\Delta t_{RL}$ can be, for example, the time period between the starting air-fuel ratio represented by the point 128a, and the actual air-fuel ratio represented by the point 126b.

Figure 3:
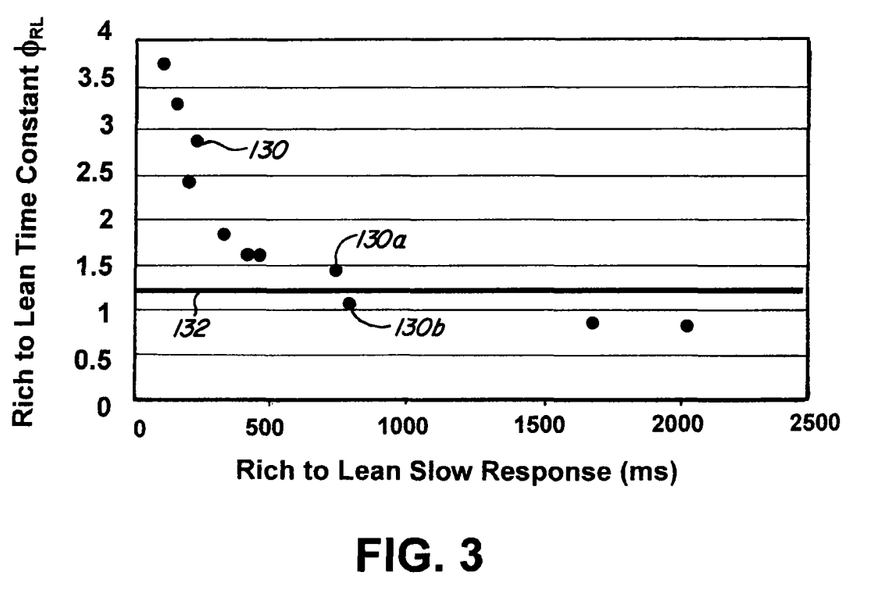
FIG. 3 depicts a graph of an exhaust gas sensor slow response according to an embodiment of the present invention.

The time constant $\phi_{RL}$ for the rich to lean fuel operation for each of a plurality of output cycles can be compared to a predetermined time constant threshold as indicated, for example, by the graph in FIG. 3. FIG. 3 depicts, for example, a plurality of time constants $\phi_{RL}$, as indicated by the points 130, are calculated for multiple output cycles. The processor 112 can compare the time constants $\phi_{RL}$ to the predetermined time constant threshold as indicated by a curve 132. Thus, for example, the time constant indicated by the point 130a is above the curve 132.

This indicates that the time constant corresponding to the point 130a is greater than the predetermined time constant threshold. Therefore, the exhaust gas sensor 108 has not malfunctioned and the processor 112 can make such a determination. However, the time constant indicated by the point 130b is below the curve 132. This indicates that the time constant corresponding to the point 130b is less than the predetermined time constant threshold. Therefore, the exhaust gas sensor 108 has malfunctioned and the processor 112 can make such a determination.

For example, to calculate the time constant for a lean to rich fuel operation $\phi_{LR}$ from point 126a to point 128a, the target air-fuel ratio $\lambda_{RT\,arg\,et}$, the minimum air-fuel ratio $\lambda_{min}$, the maximum air-fuel ratio $\lambda_{max}$ and the time period $\Delta t_{LR}$ between detection of the minimum air-fuel ratio $\lambda_{min}$ and the maximum air-fuel ratio $\lambda_{max}$ can be utilized. The target air-fuel ratio $\lambda_{RT\,arg\,et}$ can be indicated, for example, by the point 136a representing the minimum air-fuel ratio of the optimal air-fuel ratio data in the curve 116. The minimum air-fuel ratio $\lambda_{min}$ can be, for example, an actual air-fuel ratio represented by the point 128a. The maximum air-fuel ratio $\lambda_{max}$ can be, for example, a starting air-fuel ratio represented by the point 126a. The time period $\Delta t_{LR}$ can be, for example, the time period between the starting air-fuel ratio represented by the point 126a, and the actual air-fuel ratio represented by the point 128a.

Figure 4:
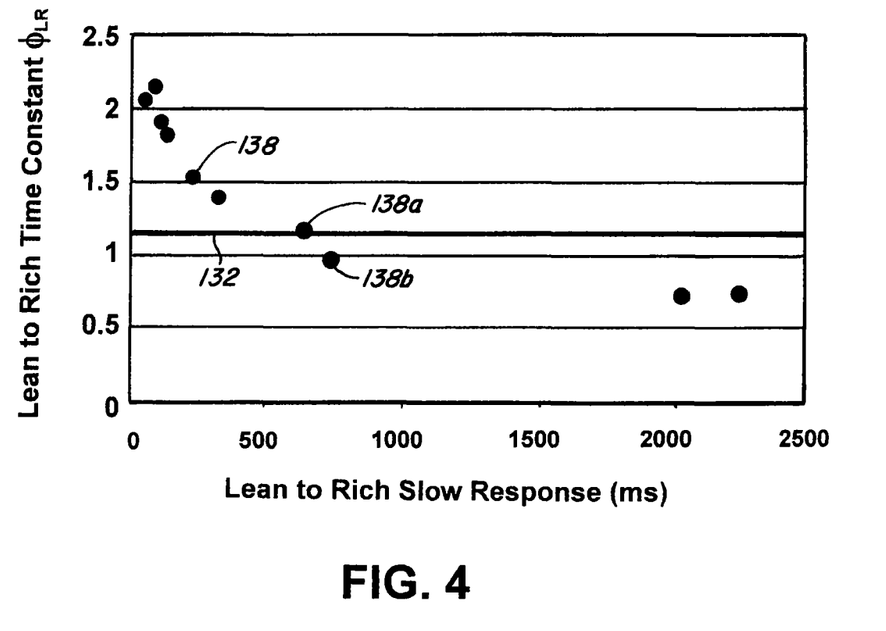
FIG. 4 depicts a graph of an exhaust gas sensor slow response according to an embodiment of the present invention.

The time constant $\phi_{LR}$ for the lean to rich fuel operation for each of a plurality of output cycles can be compared to a predetermined time constant threshold as indicated, for example, by the graph in FIG. 4. FIG. 4 depicts, for example, a plurality of time constants $\phi_{LR}$ as indicated by the points 138 are calculated for multiple output cycles. The processor 112 can compare the time constants $\phi_{LR}$ to the predetermined time constant threshold as indicated by a curve 132. Thus, for example, the time constant indicated by the point 138a is slightly above the curve 132.

This indicates that the time constant corresponding to the point 138a is greater than the predetermined time constant threshold. Therefore, the exhaust gas sensor 108 has not malfunctioned and the processor 112 can make such a determination. However, the time constant indicated by the point 138b is below the curve 132. This indicates that the time constant corresponding to the point 138b is less than the predetermined time constant threshold. Therefore, the exhaust gas sensor 108 has malfunctioned and the processor 112 can make such a determination.

In one embodiment, the predetermined time constant threshold can be adjusted based on government and/or automobile manufacturer specifications. In another embodiment, the average value of the time constant $\phi_{RL}$ for the rich to lean fuel operation instead of or in addition to the individual time constants can be compared to the predetermined time constant threshold to determine whether the exhaust gas sensor 108 has malfunctioned. Likewise, the average value of the time constant $\phi_{LR}$ for the lean to rich fuel operation instead of or in addition to the individual time constants can be compared to the predetermined time constant threshold to determine whether the exhaust gas sensor 108 has malfunctioned.

In another embodiment, a number of times that the time constant $\phi_{RL}$ for the rich to lean fuel operation falls below the predetermined time constant threshold can be used to determine whether the exhaust gas sensor 108 has malfunctioned or not. Likewise, a number of times that the time constant $\phi_{LR}$ for the lean to rich fuel operation falls below the predetermined time constant threshold can be used to determine whether the exhaust gas sensor 108 has malfunctioned or not.

In one embodiment, 6 output cycles can be used to determine whether the exhaust gas sensor 108 has malfunctioned or not. However, it is understood that any number of output cycles (more than 6 or less than 6) can be used to determine whether the exhaust gas sensor 108 has malfunctioned or not. Generally, however, the present invention provides for a reduced amount of output cycles (i.e., 6 or less) that need to be used to determine malfunctions in the exhaust gas sensor 108. With a reduced number of output cycles for determination of malfunctions, there is an increased likelihood that such a determination of malfunctions will actually be completed instead of being interrupted. This can reduce the occurrences of incomplete data, which may be undesirable.

Figure 5:
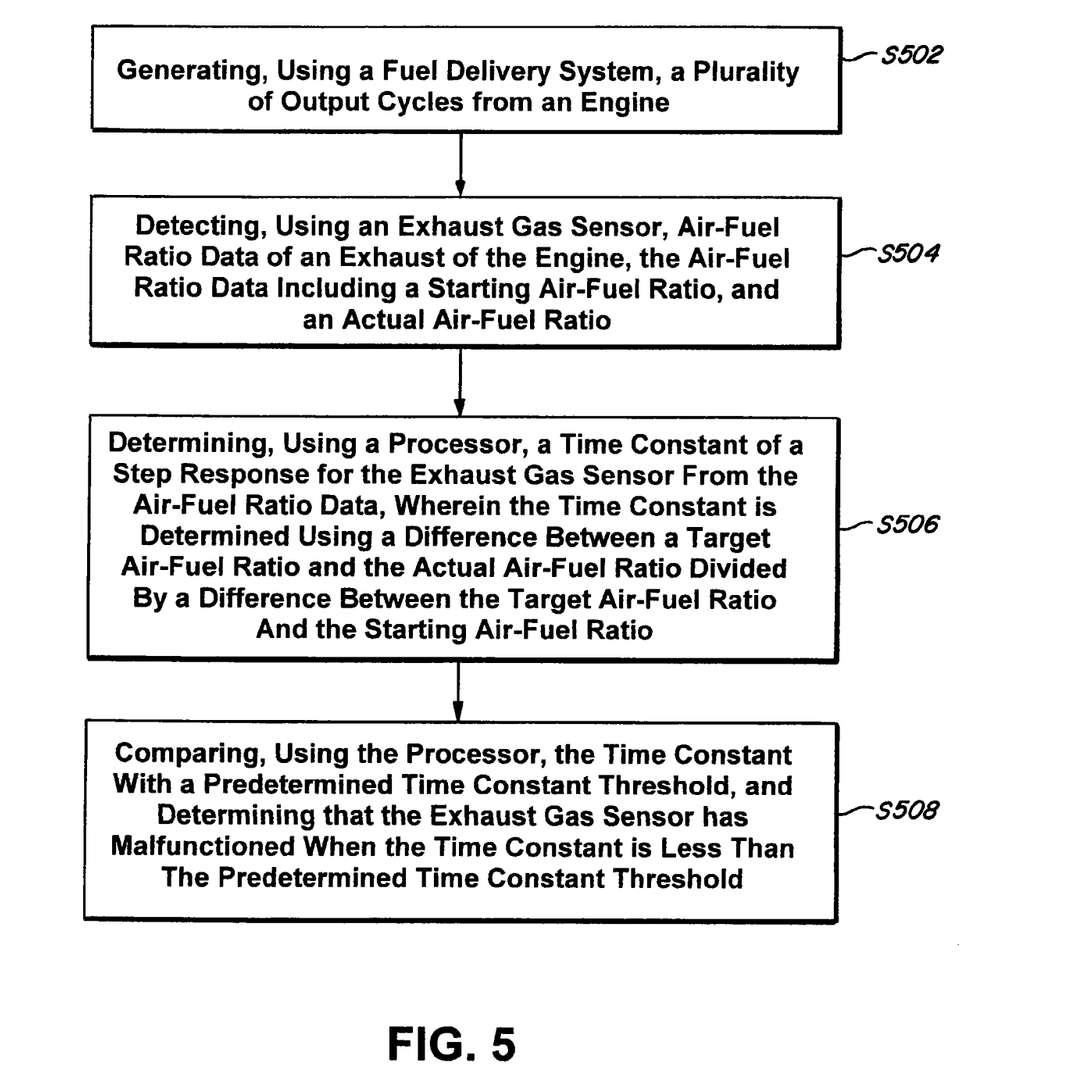
FIG. 5 depicts a process according to an embodiment of the present invention.

In one embodiment, the present invention is a process as shown in FIG. 5. In Step S502, a plurality of output cycles are generated from an engine using a fuel delivery system. For example, the fuel delivery system 104 can supply fuel in a manner to cause the engine 106 to generate exhausts in output cycles. In Step S504 air-fuel ratio data of an exhaust of the engine is detected using the exhaust gas sensor. The air-fuel ratio data can include a starting air-fuel ratio and an actual air-fuel ratio. For example, the exhaust gas sensor 108 can detect, for example, air-fuel ratio data including a starting air-fuel ratio and an actual air-fuel ratio.

In Step S506, a time constant of a step response for the exhaust gas sensor from the air-fuel ratio data is determined using a processor. The time constant is determined using a difference between a target air-fuel ratio and the actual air-fuel ratio divided by a difference between the target air-fuel ratio and the starting air-fuel ratio. For example, the processor 112 can determine the constant of a step response for the exhaust gas sensor 108 using a difference between a target air-fuel ratio and the actual air-fuel ratio divided by a difference between the target air-fuel ratio and the starting air-fuel ratio.

In Step S508, the processor compares the time constant with a predetermined time constant threshold and can determine that the exhaust gas sensor has malfunctioned when the time constant is less than the predetermined time constant threshold. For example, the processor 112 can compare the time constant with a predetermined time constant threshold and can determine that the exhaust gas sensor 108 has malfunctioned when the time constant is less than the predetermined time constant threshold.

Those of ordinary skill would appreciate that the various illustrative logical blocks, modules, and algorithm steps described in connection with the examples disclosed herein may be implemented as electronic hardware, computer software, or combinations of both. Furthermore, the present invention can also be embodied on a machine readable medium causing a processor or computer to perform or execute certain functions.

To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosed apparatus and methods.

The various illustrative logical blocks, units, modules, and circuits described in connection with the examples disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the examples disclosed herein may be embodied directly in hardware, in a software module executed by a processor, or in a combination of the two. The steps of the method or algorithm may also be performed in an alternate order from those provided in the examples. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an Application Specific Integrated Circuit (ASIC). The ASIC may reside in a wireless modem. In the alternative, the processor and the storage medium may reside as discrete components in the wireless modem.

The previous description of the disclosed examples is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A method for determining whether an exhaust gas sensor has malfunctioned, the method comprising:
   detecting, using the exhaust gas sensor, air-fuel ratio data of an exhaust of an engine, the air-fuel ratio data including a starting air-fuel ratio and an actual air-fuel ratio;

determining, using a processor, a time constant of a step response for the exhaust gas sensor from the air-fuel ratio data, the time constant being determined based on a difference between a target air-fuel ratio and the actual air-fuel ratio and a difference between the target air-fuel ratio and the starting air-fuel ratio; and comparing, using the processor, the time constant with a predetermined time constant threshold, and determining that the exhaust gas sensor has malfunctioned when the time constant is less than the predetermined time constant threshold.

2. The method of claim 1 wherein the time constant is determined using the difference between the target air-fuel ratio and the actual air-fuel ratio divided by the difference between the target air-fuel ratio and the starting air-fuel ratio.

3. The method of claim 1 further comprising generating, using a fuel delivery unit, a plurality of output cycles of the engine.

4. The method of claim 3 wherein:

each of the plurality of output cycles of the engine includes a maximum air-fuel ratio and a minimum air-fuel ratio, the actual air-fuel ratio corresponds to either the minimum air-fuel ratio or the maximum air-fuel ratio, and the starting air-fuel ratio corresponds to either the minimum air-fuel ratio or the maximum air-fuel ratio.

5. The method of claim 3 wherein:

each of the plurality of output cycles of the engine includes a maximum air-fuel ratio and a minimum air-fuel ratio, the actual air-fuel ratio corresponds to the maximum air-fuel ratio, and the starting air-fuel ratio corresponds to either the minimum air-fuel ratio.

6. The method of claim 3 wherein:

each of the plurality of output cycles of the engine includes a maximum air-fuel ratio and a minimum air-fuel ratio, the actual air-fuel ratio corresponds to the minimum air-fuel ratio, and the starting air-fuel ratio corresponds to the maximum air-fuel ratio.

7. The method of claim 3 wherein the time constant is determined using the formula:

$$\phi_{LR} = \frac{-\ln\left(\frac{|\lambda_{RTarget} - \lambda_{min}|}{\lambda_{max} - \lambda_{RTarget}}\right)}{\Delta t_{LR}},$$

wherein $\phi_{LR}$ is the time constant for a portion of at least one of the output cycles of the engine corresponding to a lean to rich fuel operation by the fuel delivery unit, $\lambda_{RT\,arg\,et}$ is the target air-fuel ratio corresponding to the lean to rich fuel operation by the fuel delivery unit, $\lambda_{min}$ is the minimum air-fuel ratio detected by the exhaust gas sensor corresponding to the lean to rich fuel operation by the fuel delivery unit, $\lambda_{max}$ is the maximum air-fuel ratio detected by the exhaust gas sensor corresponding to the lean to rich fuel operation by the fuel delivery unit, and $\Delta t_{LR}$ is a time period between detection of the $\lambda_{min}$ and the $\lambda_{max}$.

8. The method of claim 3 wherein the time constant is determined using the formula:

$$\phi_{RL} = \frac{-\ln\left(\frac{|\lambda_{max} - \lambda_{LTarget}|}{\lambda_{LTarget} - \lambda_{min}}\right)}{\Delta t_{RL}},$$

wherein $\phi_{RL}$ is the time constant for a portion of at least one of the plurality of output cycles of the engine corresponding to a rich to lean fuel operation by the fuel delivery unit, $\lambda_{LT\,arg\,et}$ is the target air-fuel ratio corresponding to the rich to lean fuel operation by the fuel delivery unit, $\lambda_{min}$ is the minimum air-fuel ratio detected by the exhaust gas sensor corresponding to the rich to lean fuel operation by the fuel delivery unit, $\lambda_{max}$ is the maximum air-fuel ratio detected by the exhaust gas sensor corresponding to the rich to lean fuel operation by the fuel delivery unit, and $\Delta t_{RL}$ is a time period between detection of the $\lambda_{min}$ and the $\alpha_{max}$.

9. A method for determining an exhaust gas sensor malfunction comprising:

generating, using a fuel delivery unit, a plurality of output cycles of an engine;

detecting, using an exhaust gas sensor, air-fuel ratio data of an exhaust of the engine, the air-fuel ratio data including a starting air-fuel ratio, and an actual air-fuel ratio;

determining, using a processor, a time constant of a step response for the exhaust gas sensor from the air-fuel ratio data, wherein the time constant is determined using a difference between a target air-fuel ratio and the actual air-fuel ratio divided by a difference between the target air-fuel ratio and the starting air-fuel ratio; and comparing, using the processor, the time constant with a predetermined time constant threshold, and determining that the exhaust gas sensor has malfunctioned when the time constant is less than the predetermined time constant threshold.

10. The method of claim 9 wherein the time constant is determined using the formula:

$$\phi_{LR} = \frac{-\ln\left(\frac{|\lambda_{RTarget} - \lambda_{min}|}{\lambda_{max} - \lambda_{RTarget}}\right)}{\Delta t_{LR}},$$

wherein $\phi_{LR}$ is the time constant for a portion of at least one of the plurality of output cycles of the engine corresponding to a lean to rich fuel operation by a fuel delivery unit, $\lambda_{RT\,arg\,et}$ is the target air-fuel ratio, $\lambda_{min}$ is the minimum air-fuel ratio, $\lambda_{max}$ is the maximum air-fuel ratio, and $\Delta t_{LR}$ is a time period between detection of the $\lambda_{min}$ and the $\lambda_{max}$.

11. The method of claim 9 wherein the time constant is determined using the formula:

$$\phi_{RL} = \frac{-\ln\left(\frac{|\lambda_{max} - \lambda_{LTarget}|}{\lambda_{LTarget} - \lambda_{min}}\right)}{\Delta t_{RL}},$$

wherein $\phi_{RL}$ is the time constant for a portion of at least one of the plurality of output cycles of the engine corresponding to a rich to lean fuel operation by a fuel delivery unit, $\lambda_{LT\,arg\,et}$ is the target air-fuel ratio, $\lambda_{min}$ is the minimum air-fuel ratio, $\lambda_{max}$ is the maximum air-fuel ratio, and $\Delta t_{RL}$ is a time period between detection of the $\lambda_{min}$ and the $\lambda_{max}$.

12. The method of claim 9 wherein each of the plurality of output cycles of the engine includes a maximum air-fuel ratio and a minimum air-fuel ratio.

13. The method of claim 12 wherein the actual air-fuel ratio corresponds to the minimum air-fuel ratio, and the starting air-fuel ratio corresponds to the maximum air-fuel ratio.

14. The method of claim 12 wherein the actual air-fuel ratio corresponds to the maximum air-fuel ratio, and the starting air-fuel ratio corresponds to the minimum air-fuel ratio.

15. An automobile comprising:
an engine generating an exhaust;
a fuel delivery unit connected to the engine and configured to generate a plurality of output cycles of the engine;
an exhaust gas sensor configured to detect air-fuel ratio data of the exhaust, the air-fuel ratio data including a starting air-fuel ratio, and an actual air-fuel ratio; and
a processor receiving the air-fuel ratio data and configured to:
determine a time constant of a step response for the exhaust gas sensor from the air-fuel ratio data, wherein the time constant is determined using a difference between a target air-fuel ratio and the actual air-fuel ratio divided by a difference between the target air-fuel ratio and the starting air-fuel ratio,
compare the time constant with a predetermined time constant threshold, and
determine that the exhaust gas sensor has malfunctioned when the time constant is less than the predetermined time constant threshold.

16. The automobile of claim 15 wherein each of the plurality of output cycles of the engine includes a maximum air-fuel ratio and a minimum air-fuel ratio, and the actual air-fuel ratio corresponds to the minimum air-fuel ratio, and the starting air-fuel ratio corresponds to the maximum air-fuel ratio.

17. The automobile of claim 15 wherein each of the plurality of output cycles of the engine includes a maximum air-fuel ratio and a minimum air-fuel ratio, and the actual air-fuel ratio corresponds to the maximum air-fuel ratio, and the starting air-fuel ratio corresponds to the minimum air-fuel ratio.

18. The automobile of claim 15 wherein processor determines the time constant using the formula:

$$\phi_{LR} = \frac{-\ln\left(\frac{|\lambda_{RTarget} - \lambda_{min}|}{\lambda_{max} - \lambda_{RTarget}}\right)}{\Delta t_{LR}},$$

wherein $\phi_{LR}$ is the time constant for a portion of at least one of the plurality of output cycles of the engine corresponding to a lean to rich fuel operation by a fuel delivery unit, $\lambda_{RT\ arg\ et}$ is the target air-fuel ratio, $\lambda_{min}$ is the minimum air-fuel ratio, $\lambda_{max}$ is the maximum air-fuel ratio, and $\Delta t_{LR}$ is a time period between detection of the $\lambda_{min}$ and the $\lambda_{max}$.

19. The automobile of claim 15 wherein the processor determines the time constant using the formula:

$$\phi_{RL} = \frac{-\ln\left(\frac{|\lambda_{max} - \lambda_{LTarget}|}{\lambda_{LTarget} - \lambda_{min}}\right)}{\Delta t_{RL}},$$

wherein $\phi^{RL}$ is the time constant for a portion of at least one of the plurality of output cycles of the engine corresponding to a rich to lean fuel operation by a fuel delivery unit, $\lambda_{LT\ arg\ et}$ is the target air-fuel ratio, $\lambda_{min}$ is the minimum air-fuel ratio, $\lambda_{max}$ is the maximum air-fuel ratio, and $\Delta t_{RL}$ is a time period between detection of the $\lambda_{min}$ and the $\lambda_{max}$.

* * * * *